United States Patent [19]

Minkowitz

[11] 4,347,081

[45] Aug. 31, 1982

[54] DENTAL ALLOY

[75] Inventor: Arthur Minkowitz, Albertson, N.Y.

[73] Assignee: Futura Dental Products, Inc., Long Island City, N.Y.

[21] Appl. No.: 296,872

[22] Filed: Aug. 27, 1981

[51] Int. Cl.$^3$ ............................................. C22C 9/04
[52] U.S. Cl. ..................................... 75/157.5; 148/32
[58] Field of Search .............. 75/153, 160, 162, 157.5; 148/32

[56] References Cited

U.S. PATENT DOCUMENTS 4,094,671  6/1978  Hayashi ............................... 75/157.5

FOREIGN PATENT DOCUMENTS 44-28789  11/1969  Japan ..................................... 75/160

Primary Examiner—Peter K. Skiff
Attorney, Agent, or Firm—Auslander, Thomas & Morrison

[57]     ABSTRACT

A non-precious metal alloy for use in restorative dentistry comprising in percent weight: copper 60–66, silicon 0.60–1.65, aluminum 0.25–0.75, titanium 0.20–0.80, chromium 0.10–0.80, and zinc 33–36.

5 Claims, No Drawings

DENTAL ALLOY

The present invention relates to an alloy comprised of non-precious metals especially adapted for use in the dental field for the preparation of crowns, bridges, inlays and other dental prostheses. It is an economical alloy since it does not contain any of the higher priced metals such as gold, silver or any of the metals in the platinum family.

BACKGROUND OF THE INVENTION

The use of metals in restorative dentistry is well known. Metals, per se, or preferably alloys comprising metals used in restorative dentistry have to possess certain properties to be suitable for their intended use. In general, alloys which have been found most suitable are gold alloys or gold alloys containing platinum. These alloys have been most used because they possess an extremely high chemical stability against discoloration and dissolution in the mouth, as well as possessing preferred mechanical properties such as high extensibility, excellent workability, and high wear resistance. However, while these gold alloys have been found to be most suitable, the increasingly high price of gold is making their use economically prohibitive, and it would be desirable to provide alloys possessing the desirable properties of the presently used gold alloys but being much less expensive.

The use of alloys containing metals other than gold, silver or the metals of the platinum family in the restorative dental field is known. U.S. Pat. No. 4,094,671 describes an alloy containing 48–52% copper and 47–51% zinc as the major constituents along with a minor amount (0.1 to 1.0%) zirconium as well as other metals. U.S. Pat. No. 4,255,190 describes an alloy containing cobalt and chromium as the major constituents. This alloy is particularly suitable for adhering to low-fusing procelain.

THE PRESENT INVENTION

The present invention provides an alloy suitable for use in the centrifugal casting in refractory molds for the preparation of dental crowns, bridges, inlays and other prostheses. This alloy is comprised in percent weight of the following metals:

| | |
|---|---|
| copper | 60–66 |
| silicon | 0.60–1.65 |
| aluminum | 0.25–0.75 |
| titanium | 0.20–0.80 |
| chromium | 0.10–0.80, and |
| zinc | 33–36 |

Preferred composition consist essentially in percent weight of the following metals:

| | |
|---|---|
| copper | 61.0–64.0 |
| silicon | 0.80–1.35 |
| aluminum | 0.35–0.60 |
| titanium | 0.30–0.70 |
| chromium | 0.20–0.50, and |
| zinc | 34.50–34.95 | and have a melting range of about 1,580°–1,780° F., a density of about 0.302 lbs per cubic inch at 68° F., a specific gravity of about 8.3 to 8.5, a modulus of elasticity of about $15.5 \times 10^6$ lbs/sq in, a tensile strength of about 55,000 lbs/sq in, a yield of about 25,000 lbs/sq in, an elongation in 2 inches of about 30%, a hardness of about 105 according to the Brinell 500 kg wt, and an impact strength of about 33 Izod-foot pounds.

While alloys containing copper and one or more of the metals of the alloys of the present invention are described in several patents (U.S. Pat. Nos. 1,692,936; 1,848,857; 1,848,858; 1,933,390; 1,954,003; 2,049,449; 2,058,884; 2,075,004; 2,079,484; 2,130,737; 2,145,065; 2,157,149; and 2,175,223, none of these patents show the alloys of the present invention or discloses that any of these alloys would be suitable for use in restorative dentistry in place of the presently used gold alloys.

DETAILED DESCRIPTION OF INVENTION

The invention will become clearer from the example which follows. This example is given by way of illustration and is not to be considered as limiting.

EXAMPLE

A mixture containing:

| | |
|---|---|
| copper | 62.55 g |
| zinc | 34.75 g |
| silicon | 1.25 g |
| aluminum | 0.55 g |
| titanium | 0.55 g, and |
| chromium | 0.35 g | was melted down by heating to about 1,800° F. in a suitable vessel with agitation till a uniform melt was obtained. The mixture was cooled and the alloy was formed into pellets suitable for dental work as needed.

The resulting alloy had a gold color and essentially the same workability characteristics as possessed alloys now on the market. Extensive tests showed that the alloys of the present invention were chemically stable, under conditions resembling those found in the mouth.

What is claimed is:

1. An alloy consisting essentially of in percent weight:

| | |
|---|---|
| copper | 60–66 |
| silicon | 0.60–1.65 |
| aluminum | 0.25–0.75 |
| titanium | 0.20–0.80 |
| chromium | 0.10–0.80, and |
| zinc | 33–36. |

2. An alloy according to claim 1 consisting essentially of:

| | |
|---|---|
| copper | 61.0–64.0 |
| silicon | 0.80–1.35 |
| aluminum | 0.35–0.60 |
| titanium | 0.30–0.70 |
| chromium | 0.20–0.50, and |
| zinc | 34.50–34.95. |

3. An alloy according to claim 2 having a melting point of about 1,580° to 1,780° F.

4. An alloy according to claim 3 having a density of about 0.302 lbs per cubic inch at 68° F., a specific gravity of about 8.3 to 8.5, a modulus of elasticity of about $15.5 \times 10^6$ lbs/sq in, a tensile strength of about 55,000 lbs/sq in, a yield of about 25,000 lbs/sq in, an elongation in 2 inches of about 30%, a hardness of about 105 according to the Brinell 500 kg wt, and an impact strength of about 33 Izod-foot pounds.

5. An alloy according to claim 4 consisting essentially of in weight percent:

| | |
|---|---|
| copper | 62.55 |
| zinc | 34.75 |
| silicon | 1.25 |
| aluminum | 0.55 |
| titanium | 0.55, and |
| chromium | 0.35. |

* * * * *